United States Patent [19]

Hardy et al.

[11] 4,174,343

[45] Nov. 13, 1979

[54] PENTAERYTHRITYL DIPHOSPHONATE-AMMONIUM POLYPHOSPHATE COMBINATIONS AS FLAME RETARDANTS FOR OLEFIN POLYMERS

[75] Inventors: William B. Hardy, Bound Brook; Tae B. Min, Piscataway; Joseph A. Hoffman, Bridgewater, all of N.J.

[73] Assignee: American Cyanamid Company, Stamford, Conn.

[21] Appl. No.: 903,294

[22] Filed: May 5, 1978

[51] Int. Cl.$^2$ ............ C07C 121/00; C08K 3/32; C08K 5/53
[52] U.S. Cl. ............ 260/45.75 B; 260/45.7 P; 260/45.7 R; 260/45.75 D; 260/45.75 F; 260/45.75 W; 260/45.8 R; 260/45.9 KA; 260/45.9 NP; 260/927 R; 260/940; 260/45.75 V
[58] Field of Search .......... 260/940, 45.8 R, 45.9 NP, 260/927 R

[56] References Cited

U.S. PATENT DOCUMENTS

| | | | |
|---|---|---|---|
| 2,632,019 | 3/1953 | Ladd | 260/940 |
| 3,090,799 | 5/1963 | Wahl et al. | 260/927 R |
| 3,141,032 | 7/1964 | Friedman | 106/15 FP |
| 3,257,337 | 6/1966 | Schoepfle et al. | 260/2 P |
| 3,332,889 | 7/1967 | Epstein et al. | 260/45.9 NP |
| 3,649,591 | 3/1972 | Murray et al. | 260/45.9 NP |
| 3,663,502 | 5/1972 | Murray et al. | 260/45.9 NP |
| 3,947,276 | 3/1976 | Siclari et al. | 106/15 FP |
| 3,978,167 | 8/1976 | Albright | 260/927 R |
| 4,073,767 | 2/1978 | Birum | 260/927 R |

OTHER PUBLICATIONS

Saunders et al., Jour. Chem. Soc., 1948, pp. 699–703.

*Primary Examiner*—Harold D. Anderson
*Assistant Examiner*—R. A. White
*Attorney, Agent, or Firm*—Bruce F. Jacobs

[57] ABSTRACT

Self-extinguishing, non-dripping polyolefin polymer compositions are prepared from a mixture of certain pentaerythrityl diphosphonates and ammonium phosphate. Dicyanopentaerythrityl diphosphonate, a new compound, is useful herein without the polyphosphate.

17 Claims, No Drawings

PENTAERYTHRITYL DIPHOSPHONATE-AMMONIUM POLYPHOSPHATE COMBINATIONS AS FLAME RETARDANTS FOR OLEFIN POLYMERS

The present invention relates in general to flame retardant polyolefin compositions and, in particular, to flame retardant polyolefin compositions containing effective flame retarding amounts of a combination of a pentaerythrityl diphosphonate and ammonium polyphosphate.

The production of compositions which are flame retardant is of considerable commercial importance in that many articles such as castings, moldings, and laminates are required to be flame resistant. At least as important as the ability to resist burning is the resistance of such compositions to drip flaming particles when they do burn, in order to prevent ignition of surrounding combustible materials, such as carpeting, draperies, or upholstery. Thus, polyolefin compositions need to be both self-extinguishing and nondripping.

The present invention is directed to polyolefin compositions, particularly polypropylene compositions, which are rendered flame retardant (i.e., both self-extinguishing and nondripping) by the incorporation therein of a flame retardant amount of a combination of a pentaerythrityl diphosphonate and ammonium polyphosphate.

The pentaerythrityl diphosphonate used herein may be represented by the formula:

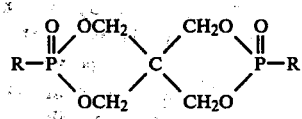

where R is methyl, phenyl, benzyl, or cyano.

Pentaerythrityl diphosphonates represented by the above formula where R is alkyl of 1 to 18 carbon atoms are disclosed by U.S. Pat. No. 3,141,032. The disclosure states that compounds where R is alkyl of at least 8 carbon atoms are preferred and that the compounds are useful as flame retardants for polyolefins.

A broader genus of pentaerythrityl diphosphonates, useful as flame retardants for polyesters, is disclosed in German Offenleg. No. 2,630,693 wherein, in the above formula, R is selected from alkyl of 1 to 10 carbon atoms, cycloalkyl of 5 to 7 carbon atoms, haloalkyl of 1 to 3 carbon atoms, alkenyl of 2 to 10 carbon atoms, phenyl or halogen-substituted phenyl, phenylalkyl (or ring halogen-substituted phenylalkyl) of 7 to 9 carbon atoms or phenylalkenyl (a ring halogen-substituted phenylalkenyl) of 8 to 10 carbon atoms.

The diphosphonates have not been found to be useful by themselves in polyolefins to provide self-extinguishing, nondripping compositions. The compositions of the present invention, to the contrary, provide self-extinguishing, non-dripping polyolefin compositions, particularly polypropylene, whereas structurally closely related compositions do not.

The pentaerythrityl diphosphonate compounds may be readily prepared by known procedures. The methyl and phenyl derivatives may be prepared by reacting, respectively, methylphosphonic dichloride and phenylphosphonic dichloride with pentaerythritol in methylene chloride or dioxane solvent at about 50° C., or in the absence of a solvent.

The compounds in general may be prepared via an Arbuzov-type rearrangement, in the presence or absence of a solvent, e.g. dioxane, by reacting an appropriate active halogen compound, e.g. benzyl chloride (bromide), with a suitable dialkyl pentaerythrityl diphosphite, e.g. diethyl pentaerythrityl diphosphite:

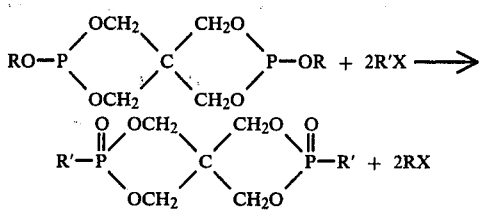

In addition to a pentaerythrityl diphosphonate compound, the flame retardant compositions further contain ammonium polyphosphate which may be prepared as described in U.S. Pat. Nos. 3,423,343 and 3,513,114. The ammonium polyphosphates are generally substantially water-insoluble and possess a plurality of P-O-P type linkages. Ammonium polyphosphate is available as Phos-chek P/30 from Monsanto Chemical Co. and has about 30% phosphorus.

The pentaerythrityl diphosphonate and the ammonium polyphosphate combination is useful as a flame retardant when incorporated into polyolefins, especially polypropylene, in a flame retarding amount, i.e., from about 20 to about 40 percent by weight, based on the weight of the polymer. The ratio of pentaerythrityl diphosphonate to ammonium polyphosphate preferably ranges from about 3:1 to 1:2 to provide the self-extinguishing, nondripping formulations of the present invention.

In order to further improve on the nondripping characteristics of the combination of pentaerythrityl diphosphonate and ammonium polyphosphate, it has been found that the addition of various oxides and/or carbonates may be especially useful.

The oxides or carbonates may be added to the polyolefin in an amount ranging from about 0.25 to 5 percent by weight, based on the weight of the polymer. Useful compounds include alkali metal carbonates, such as sodium carbonate, potassium carbonate, etc.; alkaline earth metal oxides, such as barium oxide, magnesium oxide, etc.; alkaline earth metal carbonates, such as magnesium carbonate, calcium carbonate, etc.; Group IV-A metal oxides, such as silicon dioxide, stannic oxide, etc.; titanium dioxide, zinc oxide, aluminum oxide, antimony oxide, and the like.

The polyolefins to be flame retarded herein include homopolymers and copolymers of olefins, preferably having about 2-4 carbon atoms, and particularly propylene polymers, especially homopolypropylene. Copolymers of propylene with ethylene, butylene, and isobutylene, containing 50-90 percent propylene by weight, may also be flame retarded with this invention.

The flame retardant combination may be added to the polymer as such, or as individual components, by any standard method, such as by milling the polymer and the components on, for example, a two-roll mill, in a Banbury mixer, by molding the components and the polymer simultaneously, or by extruding the polymer and components, or by merely blending all the ingredients together in powder form and thereafter forming the desired ultimate product. Additionally, the flame retardant components or combination may be added during the production of the polymer, i.e. during polymerization, provided the catalyst, conditions, and other ingredients of the polymerization are inert thereto.

It is also within the scope of this invention to incorporate such common ingredients as plasticizers, dyes, pigments, heat and light stabilizers, antioxidants, antistatic agents, photochromic materials, and the like, into the polymer composition.

EXAMPLE 1

Preparation of Dimethyl Pentaerythrityl Diphosphonate

Methylphosphonic dichloride (53.2 grams, 0.4 mole) was reacted with pentaerythritol (27.2 grams, 0.2 mole) at 55°-60° C. under a nitrogen atmosphere. The desired product was obtained in 48 percent yield; m.p. 217° C.

EXAMPLE 2

Preparation of Diphenyl Pentaerythrityl Diphosphonate

To one liter of dioxane was added 68 grams (0.5 mole) of pentaerythritol and then 174 grams (2.2 moles) of pyridine was added. Then 195 grams (1.0 mole) of phenylphosphonic dichloride was added slowly. The mixture along with all the solid precipitate was refluxed overnight with stirring. The solids were filtered and washed with cold dioxane, then slurried in one liter of water and filtered (three times), vacuum dried at 100° C., then recrystallized from dimethylformamide. Yield 140 grams (74%), m.p. 260°-262° C.

Theory for $P_2O_6C_{17}H_{18}$: C, 53.8; H, 4.79; P, 16.35. Found: C, 53.31; H, 4.78; P. 16.11.

EXAMPLE 3

Preparation of Dibenzyl Pentaerythrityl Diphosphonate

Diethyl pentaerythrityl diphosphite (0.1 mole) was reacted with benzyl chloride (0.3 mole) under a nitrogen atmosphere at 165° C. The product had a melting point of 248° C., 42% yield.

EXAMPLE 4

Preparation of Dicyano Pentaerythrityl Diphosphonate

Cyanogen bromide (0.2 mole) was reacted with diethyl pentaerythrityl diphosphite (0.1 mole) in 150 ml of dioxane at 15° C. under a nitrogen atmosphere to give the desired compound in 43% yield; m.p. 300° C. (dec.).

EXAMPLES 5-11

Following the basic procedure of Example 4, except that the solvent was omitted, diethyl pentaerythrityl diphosphite was reacted with the appropriate halide at the indicated temperatures to give compounds having the following structure wherein the R groups are as shown in Table I:

$$R-P\begin{array}{c}O\\||\\\\\\\end{array}\begin{array}{c}OCH_2\\\\\\OCH_2\end{array}C\begin{array}{c}CH_2O\\\\\\CH_2O\end{array}\begin{array}{c}O\\||\\P-R\\\\\end{array}$$

TABLE I

| Example | R | T°C. | M.P. °C. | Yield, % |
|---|---|---|---|---|
| 5 | $CH_3$—⟨⟩—$CH_2$— | 120 | 240 | 76 |
| 6 | $CH_3$—⟨⟩—$CH_2$— (with CH₃) | 120 | 196 | 69 |
| 7 | $CH_3$—⟨⟩—$CH_2$— (with 2 CH₃) | 145 | 155 | 82 |
| 8 | naphthyl-$CH_2$— | 170 | 207 | 69 |
| 9 | Cl—⟨⟩—$CH_2$— | 147 | 220 | 59 |
| 10 | Br—⟨⟩—$CH_2$— | 120 | 257 | 71 |
| 11 | $CH_2$=CH—$CH_2$— | 95 | 150 | 52 |

EXAMPLES 12-15

To evaluate the effectiveness of the flame retardant compositions of the present invention, the specified diphosphonate (15 parts by weight) and ammonium polyphosphate (15 parts by weight) were dry blended with 70 parts by weight of polypropylene powder (Profax ® 6401 of Hercules). The blends were extruded thru a Melt Index Apparatus (described in ASTM D-1238) at 250° C. to give cylindrical polymer samples 5" in length and 0.25" diameter. Two samples of each composition were subjected to the flammability procedure, Underwriters Laboratories Test UL 94, Vertical Test Method, as described in Paragraphs 3.10-3.15, September, 1973.

Each sample, held in a vertical position, was ignited with a ¾" blue flame for 10 seconds. The flame was withdrawn and the duration of the flaming before extinguishment was recorded. When flaming ceased, the test flame was reapplied for 10 seconds. After removal of the flame, the flaming duration was again recorded.

The following were recorded:
(1) Duration of time to extinguishment for each application
(2) Whether or not the specimen dripped flaming particles which ignited a cotton swatch placed 12 inches below the specimen If a sample burned for more than 30 seconds after either application, it was considered as failing the test. The results are summarized in Table II below.

TABLE II

| Example | R | Time to Flame Extinguishment | Melt Dripping |
|---|---|---|---|
| 12 | Methyl | 0 | None |
| 13 | Phenyl | 12 | None |
| 14 | Benzyl | 0 | None |
| 15 | Cyano | 0 | None |

EXAMPLES 16-33

The procedure of Examples 12-15 was repeated using the additives in the concentrations indicated in Table III. The results are also summarized in the Table.

The results clearly show that the individual additives when used alone, with the exception of dicyano pentaerythrityl diphosphonate, are ineffective in producing self-extinguishing, non-dripping compositions.

In addition, in the preferred formulation utilizing 12 percent diphosphonate, 17 percent ammonium polyphosphate, and 1 percent titanium dioxide per 70 percent of polypropylene, only the four diphosphonates of the present invention yielded self-extinguishing, non-dripping compositions. The two preferred compounds of U.S. Pat. No. 3,141,032 (See Examples 32 and 33) failed to produce self-extinguishing, non-dripping compositions.

TABLE III

| Example | | % Diphosphonate | % Ammonium Polyphosphate | % Titanium Dioxide | Evaluation of Flammability | |
|---|---|---|---|---|---|---|
| | | | | | Time to Flame Extinguishment | Melt Dripping |
| 16 | Methyl | 30 | 0 | 0 | 7 | Dripped |
| 17 | Phenyl | 30 | 0 | 0 | 8 | Dripped |
| 18 | Benzyl | 30 | 0 | 0 | 4 | Dripped |
| 19 | Cyano | 30 | 0 | 0 | 0 | None |
| 20 | — | 0 | 30 | 0 | >60 | Failed |
| 21 | Methyl | 12 | 17 | 1 | 0 | None |
| 22 | Phenyl | 12 | 17 | 1 | 0 | None |
| 23 | Benzyl | 12 | 17 | 1 | 2 | None |
| 24 | Cyano | 12 | 17 | 1 | 23 | None |
| 25 | p-methyl-benzyl | 12 | 17 | 1 | 6 | Dripped |
| 26 | 2,4-dimethylbenzyl | 12 | 17 | 1 | 5 | Dripped* |
| 27 | 2,4,6-trimethylbenzyl | 12 | 17 | 1 | 13 | Dripped* |
| 28 | Naphthylmethyl | 12 | 17 | 1 | >60 | Failed |
| 29 | p-chlorobenzyl | 12 | 17 | 1 | 15 | Dripped* |
| 30 | p-Bromobenzyl | 12 | 17 | 1 | 2 | Dripped* |
| 31 | Allyl | 12 | 17 | 1 | >60 | Dripped* |
| 32 | n-Decyl** | 12 | 17 | 1 | 24 | Dripped* |
| 33 | n-Octodecyl** | 12 | 17 | 1 | >60 | Dripped* |

*Ignited cotton
**Preferred compounds iof U. S. 3,141,032 (Exaples 6 and 1, respectively).

What is claimed is:

1. A self-extinguishing, non-dripping composition comprising a polyolefin and a self-extinguishing, non-dripping amount of a combination of (A) a compound having the formula $$R-P(O)(OCH_2)_2C(CH_2O)_2P(O)-R$$

wherein R is selected from methyl, phenyl, benzyl and cyano, and (B) ammonium polyphosphate.

2. The composition of claim 1 wherein R is methyl.
3. The composition of claim 1 wherein R is phenyl.
4. The composition of claim 1 wherein R is benzyl.
5. The composition of claim 1 wherein R is cyano.
6. The composition of claim 1 wherein the ratio of (A):(B) is from about 3:1 to 1:2.
7. The composition of claims 1 and 6 wherein the total amount of (A) and (B) is from about 20 to 40 percent by weight of the composition.
8. The composition of claim 1 wherein the polyolefin has about 2-4 carbon atoms.
9. The composition of claim 8 wherein the polyolefin is polypropylene.
10. The composition of claim 1 further containing (C) about 0.25 to 5 percent by weight, based on the weight of the polymer to which the composition is to be added, of a compound selected from the group consisting of (1) alkali metal carbonates, (2) alkaline earth metal carbonates, (3) alkaline earth metal oxides, (4) Group IV-A metal oxides, (5) titanium dioxide, (6) aluminum oxide, (7) zinc oxide, and (8) antimony oxide.
11. The composition of claim 10 wherein (C) is titanium dioxide.
12. A self-extinguishing, non-dripping composition comprising a polyolefin and a self-extinguishing, non-dripping amount of dicyanopentaerythrityl diphosphonate.
13. The composition of claim 12 wherein the diphosphonate is present in about 20 to 40 percent by weight of the composition.
14. The composition of claim 12 wherein the polyolefin has about 2-4 carbon atoms.
15. The composition of claim 14 wherein the polyolefin is polypropylene.
16. A method of flame retarding a polyolefin comprising adding to it a self-extinguishing, non-dripping amount of a combination of (A) a compound of the formula:

$$R-P(O)(CH_2O)_2C(CH_2O)_2P(O)-R$$

wherein R is selected from methyl, phenyl, benzyl and cyano, and (B) ammonium polyphosphate.

17. Dicyanopentaerythrityl diphosphonate.

* * * * *